United States Patent
Govari

(10) Patent No.: US 11,844,603 B2
(45) Date of Patent: Dec. 19, 2023

(54) VISUALIZING A TREATMENT OF BREAST CANCER

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 92 days.

(21) Appl. No.: 16/726,372

(22) Filed: Dec. 24, 2019

(65) Prior Publication Data

US 2021/0186366 A1 Jun. 24, 2021

(51) Int. Cl.
*A61B 5/06* (2006.01)
*A61B 90/00* (2016.01)
*A61B 5/00* (2006.01)

(52) U.S. Cl.
CPC ............ *A61B 5/066* (2013.01); *A61B 5/7455* (2013.01); *A61B 90/36* (2016.02); *A61B 2090/378* (2016.02); *A61B 2090/3925* (2016.02)

(58) Field of Classification Search
CPC ....... A61B 5/066; A61B 90/36; A61B 5/7455; A61B 2090/378; A61B 2090/3925; A61B 5/062; A61B 2090/364; A61B 2034/2046; A61B 2034/2051; A61B 90/37; A61B 6/502; A61B 6/463; A61N 7/00; G16H 20/40; G16H 40/63
See application file for complete search history.

(56) References Cited

U.S. PATENT DOCUMENTS

| 5,391,199 A | 2/1995 | Ben-Haim |
| 6,239,724 B1 | 5/2001 | Doron et al. |
| 6,332,089 B1 | 12/2001 | Acker et al. |

(Continued)

FOREIGN PATENT DOCUMENTS

| JP | 2001190587 A | * | 7/2001 |
| JP | 2001190587 A2 | | 7/2001 |
| WO | 9605768 A1 | | 2/1996 |

OTHER PUBLICATIONS

Detmer et al., "3D Ultrasonic Image Feature Localization Based On Magnetic Scanhead Tracking: In Vitro Calibration and Validation", 1994, Ultrasound in Med. & Biol., vol. 20, No. 9, pp. 923-936 (Year: 1994).*

(Continued)

*Primary Examiner* — Patricia J Park
*Assistant Examiner* — Adil Partap S Virk
(74) *Attorney, Agent, or Firm* — Troutman Pepper Hamilton Sanders LLP

(57) ABSTRACT

A method includes, in a medical procedure carried out during a time interval including at least first and second time periods, receiving, for the first time period, a first electrical signal indicative of at least a first position and a first orientation of a hand-held device directing energy to one or more volumetric portions of an organ. A second electrical signal indicative of at least a second position and a second orientation of the hand-held device is received for the second time period. Based on the first and second electrical signals, a cumulative energy applied to at least one of the one or more volumetric portions is estimated. The estimated cumulative energy, of at least one of the one or more volumetric portions, is overlaid on an anatomical image of the organ.

14 Claims, 2 Drawing Sheets

(56) References Cited

U.S. PATENT DOCUMENTS

| | | | |
|---|---|---|---|
| 6,484,118 B1 | 11/2002 | Govari | |
| 6,618,612 B1 | 9/2003 | Acker et al. | |
| 6,690,963 B2 | 2/2004 | Ben-Haim et al. | |
| 9,821,174 B1 | 11/2017 | Fram et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0080334 A1* | 4/2005 | Willis | A61B 90/36 600/462 |
| 2005/0090746 A1* | 4/2005 | Ohtake | A61B 8/4254 600/447 |
| 2006/0241434 A1* | 10/2006 | Shimazaki | A61B 8/461 600/437 |
| 2006/0280287 A1 | 12/2006 | Esham et al. | |
| 2007/0078334 A1* | 4/2007 | Scully | A61B 5/06 600/424 |
| 2007/0106157 A1* | 5/2007 | Kaczkowski | A61B 8/5223 600/438 |
| 2008/0033420 A1* | 2/2008 | Nields | A61B 18/1815 606/41 |
| 2008/0253526 A1 | 10/2008 | Boyden et al. | |
| 2009/0171203 A1* | 7/2009 | Avital | A61B 18/02 606/130 |
| 2010/0137705 A1* | 6/2010 | Jensen | B82Y 25/00 600/424 |
| 2010/0234724 A1* | 9/2010 | Jacobsen | A61B 34/20 600/424 |
| 2011/0144479 A1* | 6/2011 | Hastings | A61B 5/6861 600/424 |
| 2012/0029353 A1* | 2/2012 | Slayton | A61B 8/4254 600/439 |
| 2015/0082220 A1 | 3/2015 | Lane et al. | |
| 2015/0169836 A1 | 6/2015 | Vahala et al. | |
| 2015/0176961 A1* | 6/2015 | Montag | A61B 5/062 702/94 |
| 2016/0296769 A1 | 10/2016 | Barthe et al. | |
| 2018/0296853 A1 | 10/2018 | Zeitouny et al. | |

OTHER PUBLICATIONS

Accel, "AC Magnetic Field", 2016 (Year: 2016).*
JP 2001190587 Translation (Year: 2001).*
Visa Suomi et al: "The effect of tissue physiological variability on transurethral ultrasound therapy of prostate", Arvix.org, Cornell University Library, 201 Olin Library Cornell University Ithaca, NY 14853, Nov. 7, 2018.
Extended European Search Report dated May 26, 2021, from corresponding European Application No. 20216875.3.

* cited by examiner

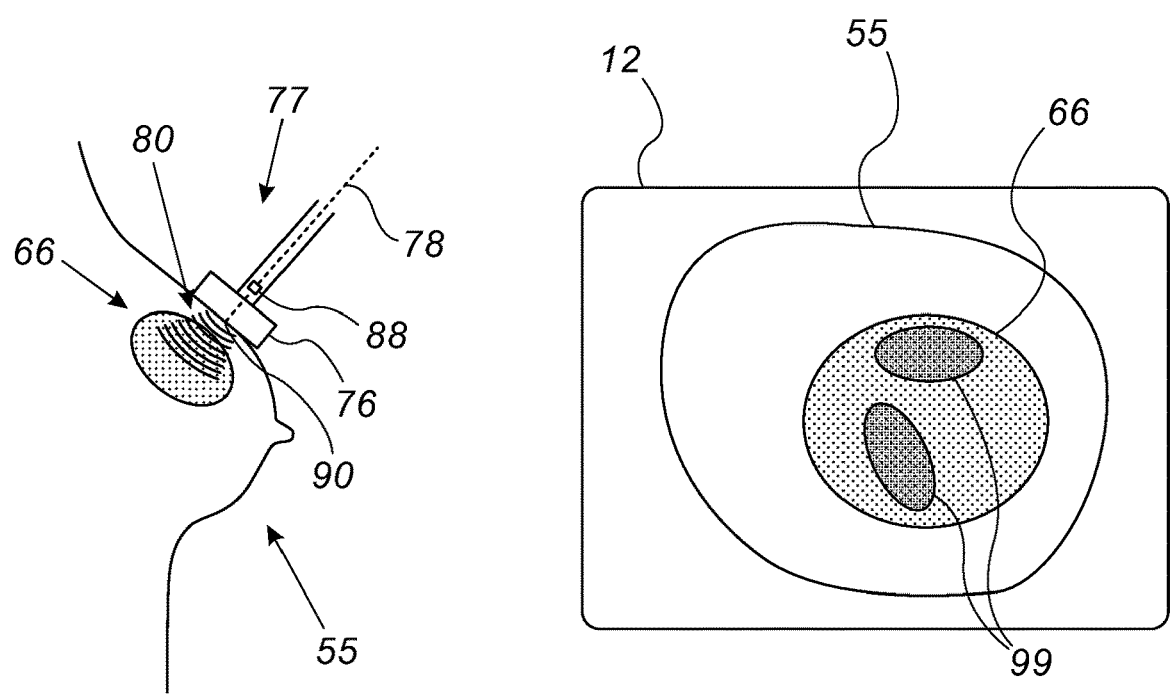
FIG. 2A
FIG. 2B
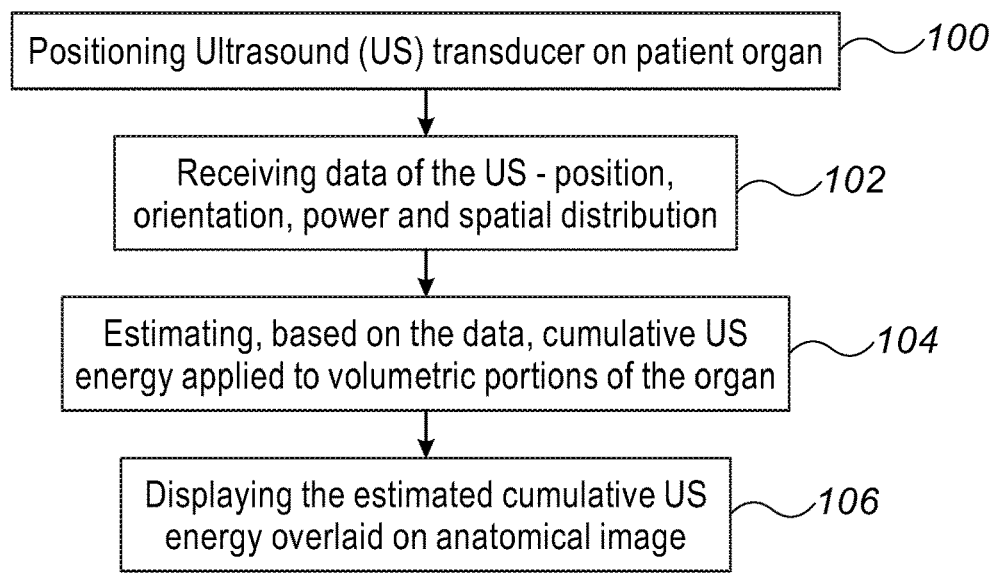
FIG. 3

VISUALIZING A TREATMENT OF BREAST CANCER

FIELD OF THE INVENTION

The present invention relates generally to medical devices, and particularly to methods and systems for visualizing a treatment of breast cancer.

BACKGROUND OF THE INVENTION

Some medical procedures, such as cancer treatment are visualized for improving the quality of the treatment.

For example, U.S. Patent application publication 2015/0169836 describes a medical instrument comprising a medical imaging system for acquiring medical image data from an imaging zone and a treatment system for depositing energy into a treatment zone. A processor executing instructions receives a selection of a reference location and one or more anatomical references. The instructions cause the processor to repeatedly: deposit energy into the subject using a treatment system; acquire medical imaging data with the medical imaging system; determine a cumulative dosage data from the medical image data; determine a first registration for the reference location; determine a second registration for the one or more anatomical references; render the medical image, the one or more anatomical references, and the cumulative dosage data in the graphical user interface; and halt the deposition of energy into the subject if a halt command is received from the graphical user interface.

U.S. Patent application publication 2015/0082220 describes methods of systems for radiotherapy. In some embodiments, the system includes a carousel for displaying the plurality of images to a user and for receiving an input from the user for selecting one or more images displayed in the carousel. A graphical user interface may be provided for displaying to the user the one or more images selected from the carousel.

SUMMARY OF THE INVENTION

An embodiment of the present invention that is described herein provides a method that includes, in a medical procedure carried out during a time interval including at least first and second time periods, receiving, for the first time period, a first electrical signal indicative of at least a first position and a first orientation of a hand-held device directing energy to one or more volumetric portions of an organ. A second electrical signal indicative of at least a second position and a second orientation of the hand-held device is received for the second time period. Based on the first and second electrical signals, a cumulative energy applied to at least one of the one or more volumetric portions is estimated. The estimated cumulative energy, of at least one of the one or more volumetric portions, is overlaid on an anatomical image of the organ.

In some embodiments, the hand-held device includes an ultrasound (US) transducer that is placed in physical contact with the organ or with a fluid applied to the organ, and receiving the first and second positions and orientations includes receiving the first and second positions and orientations of the US transducer relative to the organ. In other embodiments, at least one of the volumetric portions includes cancerous tissue, and estimating the cumulative energy includes estimating the cumulative energy that is indicative of a treatment applied to the cancerous tissue. In yet other embodiments, the method includes receiving an indication of at least one of (i) a power level of the directed energy and (ii) a spatial distribution of the directed energy applied by the hand-held device during at least one of the first and the second time periods, and estimating the cumulative energy includes assessing the cumulative energy based on the indication.

In an embodiment, the method includes holding one or more tissue parameters indicative of one or more properties of respective one or more volumetric portions of the organ, and estimating the cumulative energy includes estimating, based on the one or more tissue parameters, at least one of (i) an attenuation level and (ii) an absorption level that the directed energy undergoes in the respective one or more volumetric portions. In another embodiment, overlaying the estimated cumulative energy includes displaying a pattern depicting evolvement of the estimated cumulative energy over time.

In some embodiments, overlaying the estimated cumulative energy includes displaying a marker indicative of whether the estimated cumulative energy matches a specified level. In other embodiments, receiving the first and second electrical signals includes receiving the first and second electrical signals from a position sensor coupled to the hand-held device.

There is additionally provided, in accordance with an embodiment of the present invention, a system including a processor and a display. The processor is configured, in a medical procedure carried out during a time interval including at least first and second time periods, to: (a) receive, for the first time period, a first electrical signal indicative of at least a first position and a first orientation of a hand-held device directing energy to one or more volumetric portions of an organ, (b) receive, for the second time period, a second electrical signal indicative of at least a second position and a second orientation of the hand-held device, and (c) estimate, based on the first and second electrical signals, a cumulative energy applied to at least one of the one or more volumetric portions. The display is configured to overlay the estimated cumulative energy, of at least one of the one or more volumetric portions, on an anatomical image of the organ.

The present invention will be more fully understood from the following detailed description of the embodiments thereof, taken together with the drawings in which:

BRIEF DESCRIPTION OF THE DRAWINGS

FIG. 2A is a diagram that schematically illustrates an ultrasound-based cancer treatment procedure carried out by applying ultrasound (US) waves to a breast tumor, in accordance with an embodiment of the present invention;

FIG. 2B is a diagram that schematically illustrates a visualization of energy carried by US waves applied to a breast tumor, in accordance with an embodiment of the present invention; and FIG. 3 is a flow chart that schematically illustrates a method for determining cumulative energy applied to volumetric portions of a breast tumor during a cancer treatment procedure, in accordance with embodiments of the present invention.

DETAILED DESCRIPTION OF EMBODIMENTS

Overview

Figure 1:
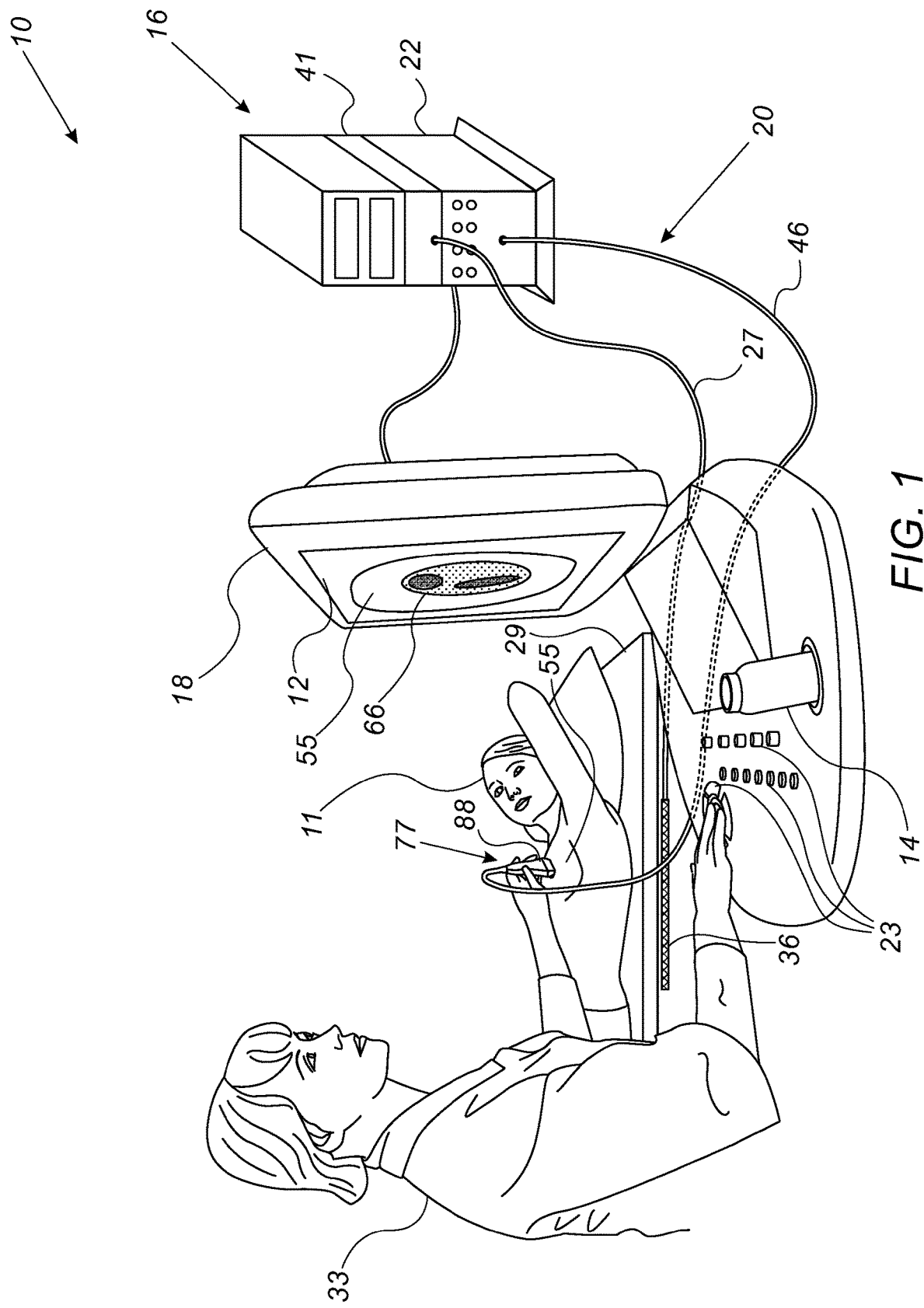
FIG. 1 is a schematic pictorial illustration of a system for treating breast cancer, in accordance with an embodiment of the present invention.

Embodiments of the present invention that are described hereinbelow provide methods and apparatus for visualizing cumulative ultrasound (US) energy applied to breast tissue during a cancer treatment procedure. In some embodiments, a system for treating breast cancer comprises an US transducer, which is configured to apply energy, carried by US waves, to breast tissue having a tumor in one or more volumetric portions thereof.

In some embodiments, a magnetic position sensor of a magnetic position tracking system, is coupled to the US transducer and is configured to produce position signals indicative of the position and orientation of the US transducer in a coordinate system of magnetic position tracking system.

During the cancer treatment procedure, a physician applies ultrasound energy to one or more volumetric portions of the breast tissue having a known tumor, so as to reduce or eliminate the tumor, e.g., by provoking the immune system to destroy the tumor.

In some embodiments, the physician sets the US transducer to apply to the breast tissue predefined parameters of the US waves, such as power, amplitude, and spatial distribution. The physician controls the US transducer to apply the US waves using a predefined amplitude and during a predefined time interval.

In some embodiments, the physician may apply the US waves by positioning the US transducer at least at two different positions on the breast skin, referred to herein as first and second positions. In such embodiments, during the time interval, the physician may apply the US waves at the first and second positions during respective first and second time periods of the time interval.

In some embodiments, the magnetic position sensor is configured to produce for the first time period, a first electrical signal indicative of a first position and a first orientation of the US transducer directing the US waves to the one or more volumetric portions of the breast tissue. The magnetic position sensor is further configured to produce for the second time period, a second electrical signal indicative of a second position and a second orientation of the US transducer.

In some embodiments, the system comprises a processor, which is configured to hold one or more tissue parameters indicative of properties of the tumor, and predefined parameters of the US waves. The processor is configured to estimate or assess, based on the first and second electrical signals and on the aforementioned tumor properties and predefined parameters of the US waves, the cumulative energy applied to one or more volumetric portions of the tumor.

In some embodiments, the processor is configured to receive, from a medical imaging system, an anatomical image of at least the tumor, and to display the anatomical image on a display of the system. In some embodiments, the processor is configured to register between coordinate systems of the medical imaging system and the magnetic position tracking system, and to overlay, on the anatomical image, the estimated cumulative energy applied to one or more of the volumetric portions of the tumor.

The disclosed techniques improve the quality of cancer treatment procedures by providing the physician with a real-time animation indicative of the cumulative energy applied to one or more volumetric portions of respective tumors. The disclosed techniques assist the physician with applying the specified dose planned for each volumetric portion, and reduce the procedure cycle-time and allocated resources, such as supplementary imaging of the respective tumors during the procedure.

System Description

FIG. 1 is a schematic pictorial illustration of a system 10 for treating breast cancer, in accordance with an embodiment of the present invention. In some embodiments, system 10 comprises a hand-held device, referred to herein as a device 77, which is operated by a physician 33 during a breast cancer treatment procedure.

In some embodiments, device 77 is configured to direct energy, in the present example the energy is carried by ultrasound (US) waves, to a breast 55 of a patient 11, so as to reduce or eliminate a known and pre-characterized cancerous tissue, referred to herein as a tumor 66, in breast 55. The operation of device 77 is described in detail in FIG. 2A below.

In an embodiment, physician 33 may apply, between device 77 and the skin of breast 55, a gel 14 or any other suitable type of fluid, configured to convey the US waves between device 77 and tumor 66 in breast 55.

In some embodiments, a magnetic position sensor 88, of a magnetic position tracking system described herein, is coupled to device 77. Magnetic position sensor 88 is configured to produce a position signal indicative of the position and orientation of device 77 in a coordinate system of the magnetic position tracking system.

In some embodiments, device 77 is electrically connected, via an electrical cable 46, to a control console 20. In an embodiment, console 20 comprises a computer 16, and user interface (UI) devices, such as but not limited to input devices 23 and a display 18. Physician 33 may use input devices 23 for controlling the operation of device 77 and other components of system 10.

In some embodiments, computer 16 comprises a driver circuit 41, which is configured to drive, via a cable 27, multiple magnetic field-generators of a location pad 36 of the magnetic position tracking system. The magnetic field-generators (e.g., three or four magnetic field-generators in location pad 36) are configured to produce alternating magnetic fields, and magnetic position sensor 88 is configured to produce the position signal in response to the alternating magnetic fields. In an embodiment, location pad 36 is placed at a known position external to patient 11 lying on a table 29, e.g., below the patient torso or at any other suitable position.

In some embodiments, computer 16 comprises a processor 22 having suitable front end and interface circuits for receiving anatomical images of breast 55 that are acquired using a suitable medical imaging system, such as but not limited to a computerized tomography (CT) system, a magnetic resonance imaging (MRI) system, or a fluoroscopy system. The front end and interface circuits are further configured for receiving position signals from magnetic position sensor 88, and for displaying on display 18, one or more of the anatomical images and additional information that will be described in detail below.

In some embodiments, processor 22 typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

During the cancer treatment procedure physician 33 moves device 77 on the skin of breast 55, and magnetic position sensor 88 produces, at each position of device 77, the aforementioned position signal, which is indicative of the present position and orientation of device 77 at the respective position on breast 55.

As described above, processor 22 is configured to display, on display 18, an anatomical image 12 (e.g., acquired by the CT system) of breast 55 having tumor 66.

In some embodiments, based on the position signal received from magnetic position sensor 88, processor 22 is configured register between the coordinate systems of the CT system and the magnetic position tracking system, and to overlay the position and orientation of device 77 on anatomical image 12.

This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

This particular configuration of system 10 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical systems.

Visualizing Cumulative Energy Applied to Cancerous Tissue

FIG. 2A is a diagram that schematically illustrates an ultrasound-based cancer treatment procedure carried out by applying ultrasound (US) waves 80 to breast tumor 66, in accordance with an embodiment of the present invention.

In some embodiments, device 77 comprises an US transducer 76, which is positioned by physician 33 at a position 90 on the skin of breast 55. Device 77 is configured to direct energy, carried by US waves 80, to tumor 66 located within breast 55. Note that US waves 80 have predefined parameters, such as amplitude, and the duration of applying US waves 80 to tumor 66 is predefined in accordance with the procedure plan.

In an embodiment, physician 33 may apply at position 90, between US transducer 76 and the skin, gel 14 or any other suitable type of fluid, which is configured to convey US waves 80 between transducer and tumor 66 within breast 55.

As described in FIG. 1 above, during the cancer treatment procedure physician 33 moves device 77 on the skin surface of breast 55 and US transducer 76 directs US waves 80 so as to treat tumor 66. In the example of FIG. 2A, physician 33 places device 77 at position 90 and processor 22 receives, from one or more magnetic position sensors 88, the position signal indicative of position 90 and the orientation of device 77, shown schematically as a dashed line 78.

In some embodiments, processor 22 receives parameters related to US waves 80. The parameters may comprise a power level of the energy carried by US waves 80, a spatial distribution of US waves 80, a time period in which US waves 80 are applied to breast 55 at position 90, and/or any other suitable parameters related to US waves 80.

As described above, tumor 66 is already characterized before conducting the cancer treatment procedure. In some embodiments, after the characterization of breast 55 and tumor 66, processor 22 may hold tissue parameters indicative of one or more properties of one or more respective volumetric portions of tumor 66. The properties of the volumetric portions may comprise tissue density, absorption and/or attenuation of US waves 80, or any other properties.

In some embodiments, processor 22 is configured to estimate, based on the parameters of US waves 80 and the quantified properties of the respective volumetric portions, an attenuation level and an absorption level that US waves 80 undergo in the respective volumetric portions of tumor 66.

FIG. 2B is a diagram that schematically illustrates a visualization of energy carried by US waves 80 applied to breast tumor 66, in accordance with an embodiment of the present invention. In some embodiments, the visualization may be carried out on anatomical image 12 that is displayed, for example, on display 18 shown in FIG. 1 above.

In some embodiments, during the cancer treatment procedure processor 22 estimates, for each position such as position 90, the attenuation level and absorption level of US waves 80 in the respective volumetric portions of tumor 66. In such embodiments, processor 22 is configured to estimate, based on the estimated attenuation level and absorption level of US waves 80, a cumulative energy applied to one or more of the volumetric portions of tumor 66.

In some embodiments, processor 22 is configured to overlay, on anatomical image 12, the estimated cumulative energy applied to one or more of the respective volumetric portions of tumor 66.

In some embodiments, processor 22 may hold one or more thresholds indicative of one or more respective specified levels of the cumulative energy to be applied to the respective volumetric portions of tumor 66. In other words, for at least one volumetric portion of tumor 66, processor 22 holds the maximal level of allowed cumulative energy.

In some embodiments, processor 22 is configured to overlay on anatomical image 12, one or more markers indicative of fully irradiated volumetric portions (FIVPs) 99. Note that FIVPs 99 are indicating that the estimated cumulative energy matches or exceeds the specified level. In the example of FIG. 2B, processor 22 assigns, to two FIVPs 99 of tumor 66, a color indicating that the level of the estimated cumulative energy matches the specified level at FIVPs 99. In other words, when a given volumetric portion of tumor 66 is sufficiently irradiated with US waves 80 in accordance with the treatment plan, processor 22 assigns a color to the given volumetric portion in anatomical image 12, so that physician 33 may stop applying US waves 80 to that given volumetric portion.

In some embodiments, processor 22 is configured to overlay on anatomical image 12, a pattern depicting real-time or near-real-time, evolvement of the estimated cumulative energy over time. The pattern may appear as animation of colors, or may have any other suitable appearance.

In other embodiments, processor 22 may overlay on anatomical image 12, any other suitable indication that, at a given volumetric portion of tumor 66, the estimated cumulative energy matches the specified level of cumulative energy.

In yet other embodiments, processor 22 may assign a color code indicative of the level of the estimated cumulative energy relative to the specified level of cumulative energy. For example, processor 22 may assign a green color to a volumetric portion of tumor 66 having the estimated cumulative energy substantially lower than the specified level of cumulative energy, a yellow color when the estimated cumulative energy is about 50% of the specified level of cumulative energy, and a red color when the estimated cumulative energy matches the specified level of cumulative energy. Note that physician 33 control device 77 for applying US waves 80 to the volumetric portions of tumor 66 having a known tumor, so as to reduce or eliminate the tumor, e.g., by provoking the immune system of patient 11 to attack tumor 66, or by over-heating tumor 66.

FIG. 3 is a flow chart that schematically illustrates a method for determining cumulative energy applied to volumetric portions of tumor 66 during a cancer treatment procedure, in accordance with embodiments of the present invention. The method begins at a positioning step 100, with physician 33 positioning US transducer 76 of device 77 at position 90 on the skin of breast 55, and applying US waves 80 in accordance with the treatment plan. As described in FIGS. 1, 2A and 2B above, physician 33 may apply US waves 80 to one or more positions on breast 55, in addition to position 90.

At a data receiving step 102, processor 22 receives data related to US transducer 76 of device 77. The data may comprise (a) position and orientation of device 77 received from magnetic position sensor 88, (b) data related to the energy carried by US waves 80, such as but not limited to the power and spatial distribution thereof, and (c) the time period of applying US waves 80 at the respective positions (e.g., position 90 and additional positions determined by physician 33) and conditions described above.

In some embodiments, at step 102 processor 22 receives the data in real-time for every position of device 77 on the skin of breast 55. As described in FIGS. 1, 2A and 2B above, processor 22 may hold tissue parameters indicative of one or more properties of respective volumetric portions of tumor 66 that were characterized before starting the cancer treatment procedure.

At an estimation step 104, processor 22 estimates, at least based on the data received at step 102, the cumulative amount of energy (carried by US waves 80) that was applied to the volumetric portions of tumor 66, at position 90 and at additional positions on breast 55 that were selected by physician 33. In some embodiments, the estimated cumulative energy is carried out in real-time.

At a displaying step 106, processor overlays, on anatomical image 12, the estimated cumulative energy applied to tumor 66 by device 77. As described in FIGS. 2A and 2B above, processor 22 displays the estimated cumulative energy applied to one or more volumetric portions of tumor 66. In some embodiments, processor 22 is configured to display a pattern depicting real-time, or near-real-time, evolvement of the estimated cumulative energy over time.

In some embodiments, processor 22 applies color-coding or any other suitable displaying technique, to the one or more volumetric portions represented in anatomical image 12. In such embodiments, processor 22 provides physician 33 with a visualization of the estimated cumulative energy applied to the respective volumetric portions, relative to the specified level of the cumulative energy as determined in the treatment procedure plan.

In an embodiment, processor 22 may display a real-time animation of the evolving colors of the volumetric portions of tumor 66. In this embodiment, processor 22 assigned the color of FIVP 99 to a given volumetric volume that have reached the specified level of cumulative energy.

Although the embodiments described herein mainly address treatment of breast cancer, the methods and systems described herein can also be used in other applications, such as in cancer treatment of any other human organ, and/or in any treatment involving applying energy to any mammalian organ.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
in a medical procedure carried out during a time interval comprising at least first and second time periods, receiving, for the first time period, a first electrical signal indicative of at least a first position and a first orientation of an external hand-held device directing ultrasound (US) energy to one or more volumetric portions of cancerous tissue of a breast of a patient;
receiving, for the second time period, a second electrical signal indicative of at least a second position and a second orientation of the external hand-held device;
estimating, via one or more processors, a cumulative US energy applied, via the external hand-held device, to at least one of the one or more volumetric portions based on one or more properties of the cancerous tissue and one or more of power, amplitude, time period applied to the at least one volumetric portion, and spatial distribution of the directed US energy,
wherein the one or more properties of the cancerous tissue comprise one or more of tissue density, absorption and/or attenuation of the directed energy into the at least one volumetric portion; and
overlaying the first position and the first orientation of the external hand-held device and the estimated cumulative US energy, of the at least one volumetric portion, on an anatomical image of the breast;
wherein said first and second electrical signals are received from a magnetic position sensor of a magnetic position tracking system, said magnetic position sensor coupled to said external hand-held device;
wherein said first and second electrical signals are indicative of the position and orientation of said external hand-held device in a coordinate system of said magnetic position tracking system;
wherein said magnetic position tracking system is utilizing a location pad, said location pad placed at a known position external to the patient and configured to produce alternating magnetic fields;
wherein the magnetic position sensor is configured to produce the first and second electrical signals in response to the alternating magnetic fields; and
wherein based on said first and second electrical signals, coordinate systems of a CT system and the magnetic position tracking system are registered.

2. The method according to claim 1, wherein the external hand-held device comprises an US transducer that is placed in physical contact with the breast or with a fluid applied to the breast, and wherein receiving the first and second positions and orientations comprises receiving the first and second positions and orientations of the US transducer relative to the breast.

3. The method according to claim 1, wherein estimating the cumulative US energy comprises estimating the cumulative US energy that is indicative of a treatment applied to the cancerous tissue.

4. The method according to claim 1, wherein overlaying the estimated cumulative US energy comprises displaying a pattern depicting evolvement of the estimated US cumulative energy over time.

5. The method according to claim 4, wherein overlaying the estimated cumulative US energy comprises displaying a marker indicative of whether the estimated cumulative US energy matches a specified level.

6. The method according to claim 1, further comprising:
overlaying one or more markers indicative of fully irradiated volumetric portions on the anatomical image.

7. A system, comprising:
a processor, which is configured, in a medical procedure carried out during a time interval comprising at least first and second time periods, to:
 (a) receive, for the first time period, a first electrical signal indicative of at least a first position and a first orientation of an external hand-held device directing ultrasound (US) energy to one or more volumetric portions of cancerous tissue of a breast;
 (b) receive, for the second time period, a second electrical signal indicative of at least a second position and a second orientation of the external hand-held device; and
 (c) estimate a cumulative US energy applied to at least one of the one or more volumetric portions based on one or more properties of the cancerous tissue and one or more of power, amplitude, time period applied to the at least one volumetric portion, and spatial distribution of the directed energy,
  wherein the one or more properties of the cancerous tissue comprise one or more of tissue density, absorption and/or attenuation of the directed US energy into the at least one volumetric portion; and
a display, which is configured to overlay the first position and the first orientation of the external hand-held device and the estimated cumulative US energy, of the at least one volumetric portion, on an anatomical image of the breast of a patient;
wherein said first and second electrical signals are received from a magnetic position sensor of a magnetic position tracking system, said magnetic position sensor coupled to said external hand-held device;
wherein said first and second electrical signals are indicative of the position and orientation of said external hand-held device in a coordinate system of said magnetic position tracking system;
wherein said magnetic position tracking system is utilizing a location pad, said location pad placed at a known position external to the patient and configured to produce alternating magnetic fields;
wherein the magnetic position sensor is configured to produce the first and second electrical signals in response to the alternating magnetic fields; and
wherein based on said first and second electrical signals, coordinate systems of a CT system and the magnetic position tracking system are registered.

8. The system according to claim 7, wherein the external hand-held device comprises an US transducer that is that is placed in physical contact with the breast or with a fluid applied to the breast, and wherein the processor is configured to receive first and second positions and orientations of the US transducer relative to the breast.

9. The system according to claim 7, wherein the processor is configured to estimate the cumulative US energy that is indicative of a treatment applied to the cancerous tissue.

10. The system according to claim 7, wherein the processor is configured to display, on the display, a pattern depicting evolvement of the estimated cumulative US energy over time.

11. The system according to claim 10, wherein the processor is configured to display, on the display, a marker indicative of whether the estimated cumulative US energy matches a specified level.

12. The system according to claim 7, wherein the processor is configured to overlay one or more markers indicative of fully irradiated volumetric portions on the anatomical image.

13. A method for treating a cancerous tumor using ultrasonic (US) energy and magnetic position tracking, the method comprising:
producing alternating magnetic fields via a location pad associated with a magnetic position tracking system, the location pad placed at a known position external to a patient;
responsive to the alternating magnetic fields, producing, via a magnetic position sensor, one or more electrical signals;
coupling an external hand-held US device to the magnetic position sensor,
 wherein each of the one or more electrical signals is indicative of a respective position and a respective orientation of the external hand-held US device in relation to the cancerous tumor;
directing, via the external hand-held US device, US energy to one or more volumetric portions of the cancerous tumor; and
estimating, via one or more processors, a cumulative US energy applied to at least one of the one or more volumetric portions based on one or more properties of the cancerous tumor and one or more of power, amplitude, time period applied to the at least one volumetric portion, and spatial distribution of the US energy,
 wherein the one or more properties of the cancerous tumor comprise one or more of tissue density, absorption and/or attenuation of the respective US energy into the one or more volumetric portions;
overlaying a first position and a first orientation of the external hand-held US device and the estimated cumulative US energy, of the at least one volumetric portion, on an anatomical image of a breast.

14. The method according to claim 13, further comprising:
overlaying one or more markers indicative of fully irradiated volumetric portions on the anatomical image.

* * * * *